(12) United States Patent  (10) Patent No.: US 6,303,782 B1
Caron  (45) Date of Patent: Oct. 16, 2001

(54) PROCESS FOR PREPARING BENZYLNITRILES

(75) Inventor: Stéphane Caron, Groton, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/516,417

(22) Filed: Mar. 1, 2000

Related U.S. Application Data

(60) Provisional application No. 60/130,175, filed on Apr. 20, 1999.

(51) Int. Cl.$^7$ .................................................. C07D 239/00
(52) U.S. Cl. ..................... 544/242; 546/144; 546/145; 546/215; 546/330; 548/202; 548/257; 548/309.7; 548/336.1; 548/376.1; 548/505; 548/561; 549/49; 549/74; 549/426; 549/467; 549/491; 558/375
(58) Field of Search ....................... 544/242; 546/144, 546/145, 330, 215; 548/336.1, 202, 257, 309.7, 561, 376.1, 505; 549/74, 49, 467, 481, 426; 558/378

(56) References Cited

PUBLICATIONS

Stéphane Caron, Enrique Vazquez, and Jill M. Wojcik, J. Am. Chem. Soc., 122(4), 712–713, 2000.*
Loupy, et al., *Synth. Comm.*, 20, 1990, pp. 2855–2864.*
Makosza, et al., *J. Org. Chem.*, 59, 1994, pp. 6796–6799.*
Rose–Munch, et al., *J. Organomet. Chem.*, 385(1), 1990, C1–C8.*
Plevey and Sampson, *J. Chem. Soc.*, 1987, pp. 2129–2136.*
Sommer, et al., *J. Org. Chem.*, 55, 1990, pp. 4817–4821.*

* cited by examiner

*Primary Examiner*—Mukund J. Shah
*Assistant Examiner*—Thomas McKenzie
(74) *Attorney, Agent, or Firm*—Peter C. Richardson; Paul H. Ginsburg; Raymond M. Speer

(57) ABSTRACT

A process is described for preparing an aromatic compound substituted by a tertiary nitrile of Formula (1.0.0):

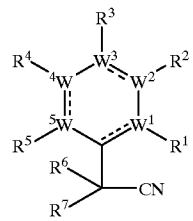

(1.0.0)

comprising treating a substituted aromatic compound of Formula (2.0.0):

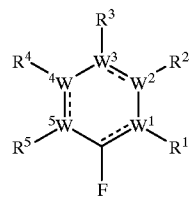

(2.0.0)

with a secondary nitrile of Formula (3.0.0):

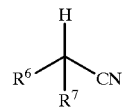

(3.0.0)

in the presence of a base having a $pK_a$ numerical value in the range of from about 17 to about 30, provided that the difference in $pK_a$ numerical values between said base and the corresponding tertiary nitrile of Formula (3.0.0) is no more than about 6; in an aprotic solvent having a dielectric constant ($\in$) of less than about 20; and at a reaction temperature in the range of from about 0° C. to about 120° C.; whereby there is formed said tertiary-nitrile-substituted aromatic compound final product of Formula (1.0.0); wherein the constituent parts $W^1$, $W^2$, $W^3$, $W^4$, and $W^5$; and the substituent moieties $R^1$, $R^2$, $R^3$, $R^4$, $R^5$, $R^6$, and $R^7$ in the compounds of Formulas (1.0.0), (2.0.0) and (3.0.0) are selected from known organic groups and radicals as further detailed in the instant specification.

10 Claims, No Drawings

PROCESS FOR PREPARING BENZYLNITRILES

REFERENCE TO RELATED COPENDING APPLICATIONS

Reference is made to provisional U.S. application Ser. No. 60/130175, filed Apr. 20, 1999 and now abandoned, benefit of the filing date of which is hereby claimed. Reference is also made to U.S. application Ser. No. 09/153,762, filed Sep. 15, 1998, now U.S. Pat. No. 6,005,118 issued Dec. 21, 1999; which is a continuation-in-part of U.S. provisional application Ser. No. 60/064211, filed Nov. 4, 1997 and now abandoned; and in corresponding European application Ser. No. 98308961.6 based on said continuation-in-part application, filed Nov. 2, 1998 and published as EP-A-0 915 089 on May 12, 1999. The above-mentioned applications are incorporated herein by reference in their entireties, and priority is claimed of the filing dates of the earliest filed of the above-mentioned applications, i.e., No. 60/064211 filed Nov. 4, 1997, and No. 60/130175 filed Apr. 20, 1999.

BACKGROUND OF THE INVENTION

The present invention relates to a novel process for preparing an aromatic compound substituted by a tertiary nitrile which is applicable to the preparation of a wide variety of compounds of this type. Such tertiary-nitrile-substituted aromatic compound final products comprise compounds of Formula (1.0.0):

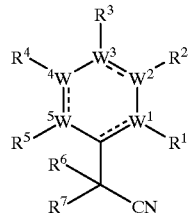

(1.0.0)

wherein: the constituent parts $W^1$, $W^2$, $W^3$, $W^4$, and $W^5$, and the substituent moieties $R^1$, $R^2$, $R^3$, $R^4$, $R^5$, $R^6$ and $R^7$ all have the meanings set out in detail further below. The process of the present invention may be illustrated by the follow reaction scheme:

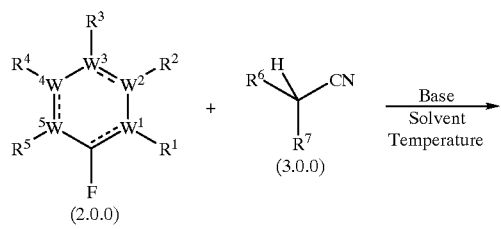

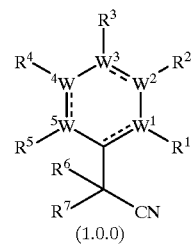

(1.0.0)

The process of the present invention is one which is both facile and which affords acceptable yields of final product. The process of the present invention is distinguished from those heretofore available by the broad scope of its applicability, and by the criticality which has been discovered relating to the chemical makeup and reaction conditions of the base used to promote the reaction, as well as of the tertiary structure of the nitrile in the final product, both of which are described in detail further below.

The character of the base which is used in carrying out the process of the present invention is critical to obtaining the acceptable yields of tertiary-nitrile-substituted aromatic compound final product which serves to distinguish the process of the present invention from the processes of the prior art. The conjugate acid of the base which is used must have a $pK_a$ in the range of from about 17 to about 30. An example of a base which meets these critical requirements is the potassium, sodium or lithium salt of bis(trimethylsilyl) amide (KHMDS).

It has also been discovered in accordance with the present invention that the type of solvent which is used to carry out the reaction between a secondary nitrile and a substituted aromatic compound represents a choice which is critical to obtaining acceptable yields of final product. The solvent selected should be aprotic and have a dielectric constant ($\in$) of less than about 20. Toluene and tetrahydrofuran (THF) are examples of suitable solvents for use in the process of the present invention. The dielectric constant of THF is 7.6 and the dielectric constant of toluene is 2.4 (*Handbook of Chemistry and Physics*).

It will be appreciated that the nitrile reactant in the method of preparation of the present invention is "secondary", referring to the degree of substitution of the carbon atom to which the nitrile moiety is attached. In the final products prepared by the method of the present invention, it will be further understood that the carbon atom to which the nitrile moiety is attached is "tertiary", since it is not attached to any hydrogen atom.

The choice of the temperature at which the reaction mixture containing the secondary nitrile and aromatic compound is to be maintained is of less critical importance than the choice of the above-mentioned base or solvent. However, the proper reaction temperature is essential to obtaining acceptable yields of final product in accordance with the present invention, and should fall within the range of from about 0° C. to about 120° C.

The tertiary-nitrile-substituted aromatic compound final products prepared in accordance with the process of the present invention are characterized by a wide range of chemical structures and by a significant number of different practical utilities, which include both therapeutic and non-therapeutic applications of the said final products.

Preferred tertiary-nitrile-substituted aromatic compound final products prepared in accordance with the process of the present invention are those which are useful as therapeutic agents, especially inhibitors of phosphodiesterase type IV (PDE4). PDE4 inhibitors have applicability in therapeutic methods of treatment in humans and animals of many diseases, illnesses and conditions which are allergic or inflammatory in origin, especially including asthma, chronic obstructive pulmonary disease, bronchitis, rheumatoid arthritis and osteoarthritis, dermatitis, psoriasis, and allergic rhinitis.

Among such PDE4 inhibitors comprising tertiary-nitrile-substituted aromatic compound final products is a preferred class of selective PDE4 inhibitors disclosed in U.S. application Ser. No. 09/406,220, filed Sep. 27, 1999, now U.S. Pat. No. 6,127,398, issued Oct. 3, 2000; which is a division of U.S. application Ser. No. 08/963,904, filed Apr. 1, 1997, which is a continuation-in-part of U.S. provisional application Ser. No. 60/016861, filed May 3, 1996, now abandoned; and disclosed in International Application Ser. No. PCT/IB97/00323 based on said provisional application, filed Apr. 1, 1997, designating the United States, and published as WO 97/42174 on Nov. 13, 1997.

The above-mentioned preferred class of selective PDE4 inhibitors may be illustrated by the following generic Formula (4.0.0):

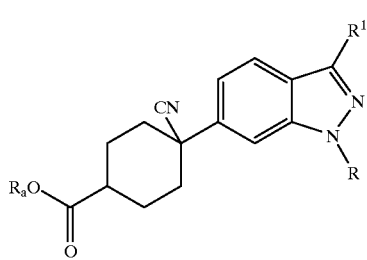

(4.0.0)

wherein $R_a$ is hydrogen, $(C_1-C_6)$ alkyl phenyl or $(C_1-C_3)$ alkyl-phenyl wherein said phenyl groups are optionally substituted by one or two —$(C_1-C_4)$ alkyl, —$O(C_1-C_3)$ alkyl, Br, or Cl; R is hydrogen, $(C_1-C_6)$ alkyl, —$(CH_2)_n(C_3-C_7)$ cycloalkyl where n is 0 to 2, or —$(Z')_b(C_6-C_{10})$ aryl where b is 0 or 1 and Z' is $(C_1-C_6)$ alkylene or $(C_2-C_6)$ alkenylene, where said alkyl and aryl moieties of said R groups are optionally substituted by one or more halo, preferably F or Cl, hydroxy, $(C_1-C_5)$ alkyl, $(C_1-C_5)$ alkoxy, or trifluoromethyl; and $R^1$ is hydrogen, $(C_1-C_6)$ alkyl phenyl, or $(C_3-C_7)$ cycloalkyl, where said alkyl and phenyl $R^1$ groups are optionally substituted with up to 3 methyl, ethyl, trifluoromethyl, or halo. Said preferred class of selective PDE4 inhibitors may be further illustrated by more preferred specific compounds of Formulas (4.0.1) and (4.0.2):

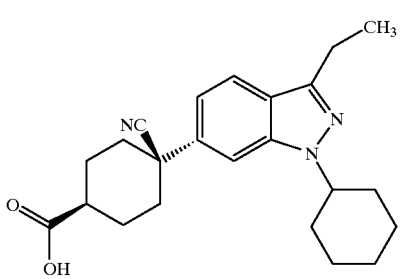

(4.0.1)

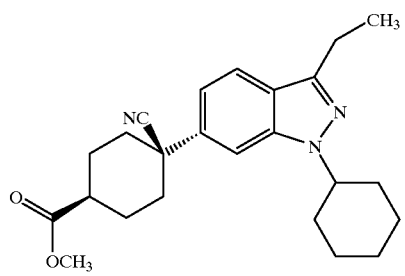

(4.0.2)

A method for preparing the above-described class of selective PDE4 inhibitors is described in U.S. application Ser. No. 09/153,762, filed Sep. 15, 1998, now U.S. Pat. No. 6,005,118 issued Dec. 21, 1999; which is a continuation-in-part of U.S. provisional application Ser. No. 60/064211, filed Nov. 4, 1997 and now abandoned; and in the corresponding European application based on said continuation-in-part application, filed Nov. 2, 1998 and published as EP-A-0 915 089 on May 12, 1999. In particular, there is disclosed in the above-mentioned applications the following synthesis procedure for treating an indazole of Formula (2.1.0) with cyclohexane 1,4-dicarbonitrile of Formula (3.1.0) to yield a tertiary-nitrile-substituted aromatic compound final product of Formula (4.0.3):

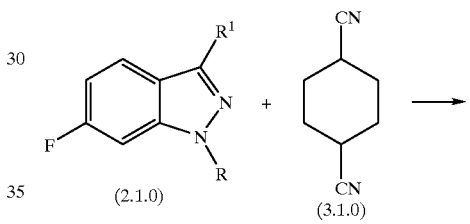

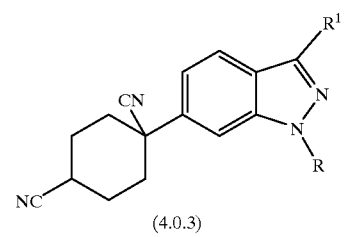

(4.0.3)

The above-illustrated synthesis procedure is described as being carried out in the presence of a base such as lithium bis(trimethylsilyl)amide, sodium bis(trimethylsilyl)amide, potassium bis(trimethylsilyl)amide (KHMDS), lithium diisopropylamide, or lithium 2,2,6,6-tetramethylpiperidine. The above-mentioned bases are described as being selective and as permitting desirably high levels of addition of cyclohexane-1,4-dicarbonitrile, Formula (2.0.1), to the R- and $R^1$-substituted indazole, Formula (2.0.0), by displacement of the fluorine atom on the latter, while retaining both carbonitrile functionalities in place. It is further taught that it is preferred to use potassium bis(trimethylsilyl)amide (KHMDS) as the base promotant, in a solvent such as tetrahydrofuran, toluene, or xylene(s), preferably toluene, at a temperature between about 25° C. and about 125° C., preferably about 100° C., for a period of from 1 hour to 15 hours, preferably about 5 hours, in order to obtain acceptable yields of a tertiary-nitrile-substituted aromatic compound final product of Formula (1.0.0).

DESCRIPTION OF THE STATE OF THE ART

Loupy et al., *Synth. Comm.*, 1990, 20, 2855–2864, is concerned with the use of solid-liquid phase transfer catalysts without solvents to carry out S$_N$Ar reactions on di- or mono-nitro halogeno compounds and unactivated aryl halides. The reaction is carried out with a nucleophile, e.g., Ph$_2$CHCN, in the presence of a base, e.g., a stoichiometric amount of pulverized solid KOH, and a catalyst, e.g., a tetraalkylammonium salt such as Aliquat 336 or TDA-1, which may be represented by the following reaction scheme:

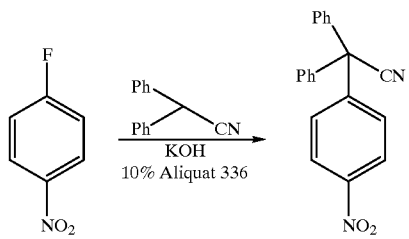

Unlike the process of the present invention, the process disclosed by Loupy et al. is carried out with a chloride-, bromide-, or fluoride-substituted arene nucleus, which is permitted by the electron deficiency of the arene nucleus caused by the additional presence of the nitro group.

Makosza et al., *J. Org. Chem.*, 1994, 59, 6796–6799, also relates to nucleophilic substitution of halogen in p-halonitrobenzenes, and discloses in particular a reaction which may be represented by the following reaction scheme:

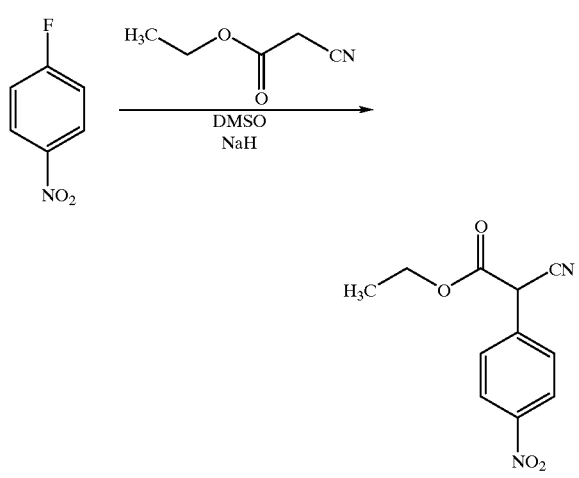

The process disclosed by Makosza et al. uses ethylcyanoacetate and may be carried out with either a chloride- or a fluoride-substituted arene nucleus. Neither of these features of the Makosza et al. process, however, can be utilized in the method of the present invention.

Rose-Munch et al., *J. Organomet. Chem.*, 1990, 385(1), C1–C3, discloses the synthesis of α-substituted aryl iminonitriles by addition of an α-iminonitrile to (fluoroarene)tricarbonylchromium complexes in the presence of a base, e.g., hexaphosphotriamide (HMPT), preceded by lithiation with, e.g., di-iso-propylaminolithium. Included in particular is a reaction which may be represented by the following reaction scheme:

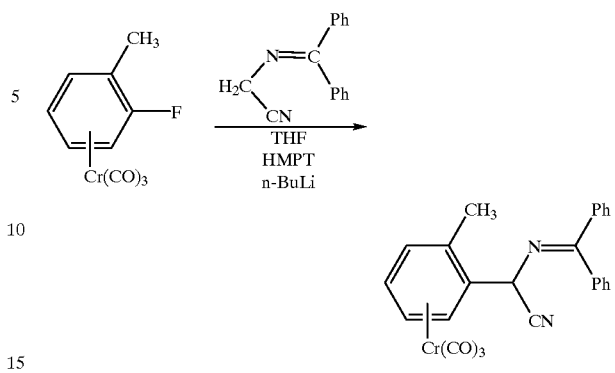

The process disclosed by Rose-Munch et al. induces an electron poor state in the fluoride-substituted arene nucleus by complexing it with tricarbonylchromium, which permits subsequent lithium anion displacement of the fluoride substituent on the arene nucleus. However, the synthetic approach of the process in Rose-Munch et al. is substantially different from that of the process of the present invention, in which lithiation is unworkable.

Plevey and Sampson, *J. Chem. Soc.*, 1987, 2129–2136 is concerned with the synthesis of 4-amino-2,3,5,6-tetrafluoroglutethimide, and as part of that preparation describes the reaction of hexafluorobenzene with ethyl cyanoacetate in the presence of potassium carbonate base, which may be illustrated by the following reaction scheme:

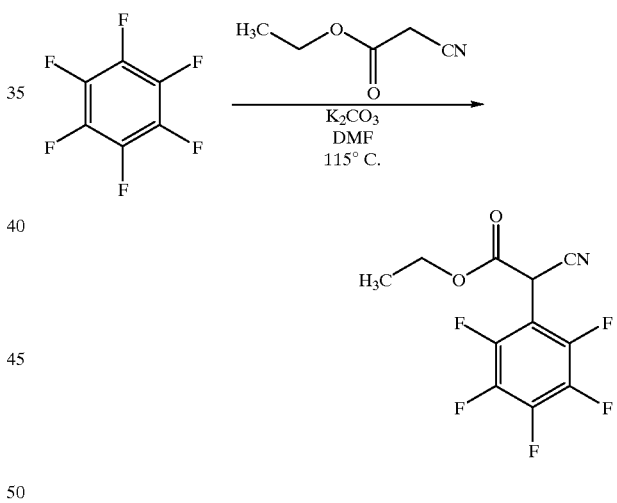

The process disclosed in Plevey and Sampson also utilizes an arene nucleus which is in an electron deficient state, as is the case with other above-described methods which characterize the current state of the art. The process of Plevey and Sampson is substantially different from that of the present invention.

Sommer et al., *J. Org. Chem.*, 1990, 55, 4817–4821, describes a process involving displacement of halogen from a 2-halogeno-substituted benzonitrile present as a stabilized carbanion, in order to prepare (2-cyanoaryl)arylacetonitriles. The process is carried out using two equivalents of a strong base, e.g., potassium tert-butoxide, and is taught to be sensitive to the nature of the base, the solvent, e.g., dimethylformamide (DMF), the leaving group, the substituents on the rings, and the kind of rings involved. The process is taught to be applicable as well to heteroaromatics with ortho-situated halogen and cyano groups. The process of Sommer et al. may be illustrated by the following reaction scheme:

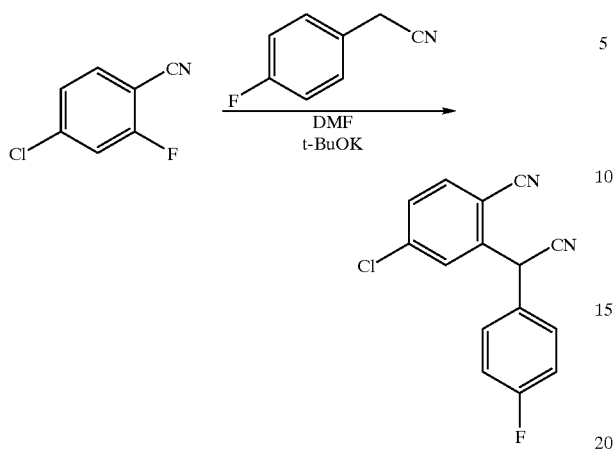

The process of Sommer et al. is substantially different from that of the present invention in that displacement of both chloride- and fluoride-substituents on the arene nucleus takes place, and further in that a secondary nitrile substituent is utilized which induces an electron poor state in the substituted arene nucleus in order to facilitate subsequent displacement.

SUMMARY OF THE INVENTION

The present invention comprises a novel method of preparing an aromatic compound substituted by a tertiary nitrile comprising: treating an aromatic compound of Formula (2.0.0):

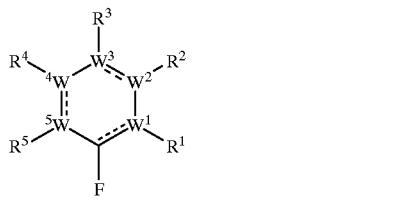

(2.0.0)

wherein: the constituent parts $W^1$, $W^2$, $W^3$, $W^4$, and $W^5$, and the substituent moieties $R^1$, $R^2$, $R^3$, $R^4$ and $R^5$ all have the meanings set out in detail further below; with a secondary nitrile of Formula (3.0.0):

(3.0.0)

wherein: the substituent moieties $R^6$ and $R^7$ both have the meanings set out in detail further below; in the presence of a base having a $pK_a$ numerical value in the range of from about 17 to about 30, provided that the difference in $pK_a$ numerical values between said base and the corresponding secondary nitrile of Formula (3.0.0) is no more than about 6; in an aprotic solvent having a dielectric constant ($\in$) of less than about 20; and at a temperature in the range of from about 0° C. to about 120° C.; whereby there is formed a tertiary-nitrile-substituted aromatic compound final product of Formula (1.0.0)

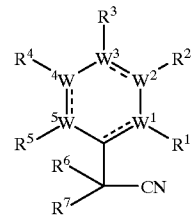

(1.0.0)

wherein $R^1$, $R^2$, $R^3$, $R^4$, $R^5$, $R^6$ and $R^7$; and $W^1$, $W^2$, $W^3$, $W^4$ and $W^5$ all have the same meanings as set out elsewhere herein.

DETAILED DESCRIPTION OF THE INVENTION

The present invention relates to a novel method of preparing an aromatic compound substituted by a tertiary nitrile. In a preferred embodiment of that method, a starting material to be treated comprises an aromatic compound of Formula (2.0.0):

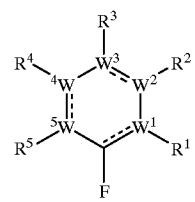

(2.0.0)

wherein:

(I) each of the dashed lines is independently absent or a bond, so that single or double bonds result at the respective positions of an aromatic compound of Formula (1.0.0) or (2.0.0), provided that at least one of said dashed lines is a bond;

(II) $W^1$, $W^2$, $W^3$, $W^4$, and $W^6$ is each independently a member selected from the group consisting of:
 (A) C (carbon) and the dashed line associated therewith is a bond;
 (B) N (nitrogen) and the dashed line associated therewith is either absent or a bond
 (C) O and the dashed line is absent;
 (D) $S(=O)_k$ where k is an integer selected from 0, 1 and 2 and the dashed line is absent; and
 (E) absent so that a 5-membered ring results; provided that each $W^1$ through $W^5$ is selected such that no more than one is absent, no more than one is O or $S(=O)_k$ optionally together with one N in each case, and no more than four are N where only N is present;

(III) $R^1$, $R^2$, $R^3$, $R^4$, and $R^5$ is each independently selected so that:
 (A) when the corresponding $W^{1-5}$ is O or $S(=O)_k$ said $R^{1-5}$ is absent;
 (B) when the corresponding $W^{1-5}$ is C said $R^{1-5}$ is a member independently selected from the group consisting of hydrogen; halogen selected from Cl, Br, and I; $-N(R^{12})_2$; $-SR^{12}$; $-OR^{12}$; $(C_1-C_6)$ alkyl substituted with 0–3 $R^9$, $-N(R^{12})_2$, $-SR^{12}$, or $-OR^{12}$; $(C_2-C_6)$ alkenyl substituted with 0–3 $R^9$; $(C_3-C_6)$ alkynyl substituted with 0–3 $R^9$; a $(C_3-C_{14})$ carbocyclic ring system substituted with 3–3 $R^9$ or 0–3 $R^{10}$; a heterocyclic ring system independently selected from the group consisting of furanyl, thienyl, pyrrolyl, imidazolyl, pyridyl, pyrazolyl, pyrimidinyl, benzofuran benzothienyl, indolyl, benzimidazolyl, tetrahydroisoquinolinyl, benzotriazolyl, and thiazolyl, said heterocyclic ring system being substituted with 0–2 $R^{10}$; and any two $R^{1-5}$ attached to adjacent carbon atoms taken together to form a 3- or 4-carbon chain forming a fused 5- or 6-membered ring, or a carbon-nitrogen-nitrogen chain forming an indazolyl fused ring, both of said rings being optionally substituted on any aliphatic carbon atoms thereof with a member selected from the group consisting of halogen selected from Cl, Br, and I; $(C_1-C_4)$ alkyl; $(C_1-C_4)$ alkoxy; and —$NR^{15}R^{16}$; where:

(1) $R^9$ is a member independently selected from the group consisting of hydrogen; cyano; —$CH_2NR^{15}R^{16}$; —$NR^{15}R^{16}$; —$R^{15}$; —$OR^{15}$; —$S(C_2-C_6)$ alkoxyalkyl; $(C_1-C_4)$ alkyl; $(C_2-C)$ alkenyl; $(C_3-C_7)$ cycloalkyl; $(C_3-C_6)$ cycloalkylmethyl; phenyl, benzyl; phenethyl; phenoxy; benzyloxy; $(C_3-C_6)$ cycloalkoxy; $(C_1-C_4)$ alkyl substituted by a member selected from the group consisting of methylenedioxy, ethylenedioxy, phenyl$(C_1-C_3)$ alkyl, and a $(C_5-C_{14})$ carbocyclic residue; and a 5- to 10-membered heterocyclic ring system containing 1 to 4 heteroatoms independently selected from oxygen, nitrogen, and sulfur, substituted with 0 to 3 substituents $R^{15}$; where:

(a) $R^{15}$ is a member selected from the group consisting of phenyl substituted by 0–3 $R^{11}$; benzyl substituted by 0–3 $R^{11}$; $(C_1-C_6)$ alkyl substituted by 0–3 $R^{11}$; $(C_2-C_4)$ alkenyl substituted by 0–3 $R^{11}$; and $(C_3-C_6)$ alkoxyalkyl substituted by 0–3 $R^{11}$;
   where $R^{11}$ is a member independently selected from the group consisting of cyano; —$CH_2NR^{18}R^{19}$; —$NR^{18}R^{19}$; $(C_3-C_6)$ alkoxyalkyl; $(C_1-C_4)$ alkyl; $(C_2-C_4)$ alkenyl; $(C_3-C_{10})$ cycloalkyl; $(C_3-C_6)$ cycloalkylmethyl; benzyl; phenethyl; phenoxy; benzyloxy; $(C_7-C_{10})$ arylalkyl; $(C_3-C_6)$ cycloalkoxy; methylenedioxy; ethylenedioxy; and a $(C_5-C_{14})$ carbocyclic residue; and a 5- to 10-membered heterocyclic ring system containing 1 to 4 heteroatoms independently selected from oxygen, nitrogen, and sulfur; where $R^{18}$ and $R^{19}$ are each independently selected from the group consisting of $(C_1-C_6)$ alkyl; and phenyl substituted with 0–3 $R^{11}$;

(b) $R^{16}$ is a member selected from the group consisting of $(C_1-C_4)$ alkyl substituted by 0–3 groups selected from the group consisting of $(C_1-C_4)$ alkoxy; $(C_2-C_6)$ alkoxyalkyl; $(C_2-C_6)$ alkenyl; phenyl; and benzyl;

(2) $R^{10}$ when a substituent on a carbon atom, is a member independently selected from the group consisting of phenyl; benzyl; phenethyl; phenoxy; benzyloxy; halogen; cyano; $(C_1-C_4)$ alkyl; $(C_3-C_7)$ cycloalkyl; $(C_3-C_6)$ cycloalkylmethyl; $(C_1-C_6)$ alkoxy; $(C_1-C_4)$ alkoxy$(C_1-C_3)$ alkyl; $(C_3-C_6)$ cycloalkoxy; $(C_1-C_6)$ alkylthio; $(C_1-C_4)$ alkylthio$(C_1-C_3)$ alkyl; —$OR^{15}$; —$NR^{15}R^6$; $(C_1-C_4)$ alkyl substituted by —$NR^{15}R^{16}$; $(C_2-C_6)$ alkoxyalkylene optionally substituted by $Si[(C_1-C_3)$ alkyl$]_3$; methylenedioxy; ethylenedioxy; —$S(O)_mR^{15}$; —$SO_2NR^{15}R^{16}$; —$OCH_2CO_2R^{15}$; —$C(R^{16})$=$N(OR^{16})$; and a 5- or 6-membered heterocyclic ring system containing from 1 to 4 heteroatoms selected from oxygen, nitrogen, and sulfur; or $R^{10}$ when a substituent on a nitrogen atom, is a member independently selected from the group consisting of phenyl; benzyl; phenethyl; $(C_1-C_4)$ alkyl; $(C_1-C_4)$ alkoxy; $(C_3-C_6)$ cycloalkyl; $(C_3-C_6)$ cycloalkylmethyl; $(C_2-C_6)$ alkoxyalkyl; —$CH_2NR^{15}R^{16}$; —$NR^{15}R^{16}$; and —$C(R^{16})$=$N(OR^{16})$;
where $R^{15}$ and $R^{16}$ have the same meaning as recited further above;

(3) $R^{12}$ is a member selected from the group consisting of $(C_1-C_6)$ alkyl substituted by 0–3 $R^9$; and $(C_3-C_6)$ alkoxyalkyl substituted by 0–3 $R^9$;
where $R^{10}$ has the same meaning as recited further above; and (C) when the corresponding $W^{1-5}$ is N said $R^{1-5}$ is a member independently selected from the group consisting of phenyl; benzyl; phenethyl; phenoxy; $(C_1-C_4)$ alkyl; $(C_1-C_4)$ alkoxy; $(C_3-C_6)$ cycloalkyl; $(C_3-C_6)$ cycloalkylmethyl; —$CH_2NR^{15}R^{16}$; —$NR^{15}R^{16}$; $(C_2-C_6)$ alkoxyalkyl; and —$C(R^{16})$=$N(OR^{16})$;
where $R^{15}$ and $R^{16}$ are as defined further above.

The above-described starting material comprising a compound of Formula (2.0.0) is reacted with a secondary nitrile of Formula (3.0.0):

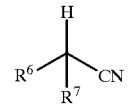

(3.0.0)

wherein: the substituent moieties $R^6$ and $R^7$ both have the meanings set out in detail below; in the presence of a base whose conjugate acid $pK_a$ is in the range of from about 17 to about 30, provided that the difference in $pK_a$ numerical values between said base and said corresponding secondary nitrile of Formula (3.0.0) is no more than about 6, and preferably no more than about 4; and in an aprotic solvent having a dielectric constant ($\in$) of less than about 20; and at a temperature in the range of from about 0° C. to about 120° C.; whereby there is formed a tertiary-nitrile-substituted aromatic compound of Formula (1.0.0):

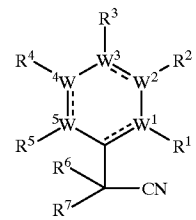

(1.0.0)

wherein $R^1$, $R^2$, $R^3$, $R^4$, $R^5$, $R^6$ and $R^7$; and $W^1$, $W^2$, $W^3$, $W^4$ and $W^5$ all have the same meanings as set out elsewhere herein.

One of the key features of the process of the present invention is that the nitrile moiety is required to be tertiary in the final product of Formula (1.0.0), and therefore as a reactant must be secondary in order of substitution, as shown in Formula (3.0.0):

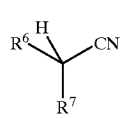
(3.0.0)

wherein $R^6$ and $R^7$ may not, accordingly, have the meaning of hydrogen. The process of the present invention produces suitable results even where $R^6$ and $R^7$ have a substantial number of different meanings. Accordingly, in the secondary nitrile reactant compounds of Formula (3.0.0):

- $R^6$ and $R^7$ are each independently selected from the group consisting of —N($R^{12}$)$_2$; ($C_1$–$C_6$) alkyl substituted with 0–3 $R^9$; —N($R^{12}$)$_2$; —$SR^{12}$; —$OR^{12}$; ($C_2$–$C_6$) alkenyl substituted with 0–3 $R^9$; ($C_3$–$C_6$) alkynyl substituted with 0–3 $R^9$; a ($C_3$–$C_{14}$) carbocyclic ring system substituted with 0–3 $R^9$ or 0–3 $R^{10}$; and a heterocyclic ring system independently selected from the group consisting of furanyl, thienyl, pyrrolyl, imidazolyl, tetrahydropyranyl, pyridyl, piperidinyl, pyrazolyl, pyrimidinyl, benzofuranyl, benzothienyl, indolyl, benzimidazolyl, tetrahydroisoquinolinyl, benzotriazolyl, and thiazolyl, said heterocyclic ring system being substituted with 0–2 $R^{10}$; or

- $R^6$ and $R^7$ are taken together to form a ($C_3$–$C_{14}$) carbocyclic ring system substituted with 0–3 $R^9$ or 0–3 $R^{10}$; phenyl; 1- or 2-naphthyl substituted with 0–3 $R^9$ or 0–3 $R^{10}$; or a heterocyclic ring system independently selected from the group consisting of furanyl, thienyl, pyrrolyl, imidazolyl, tetrahydropyranyl, pyridyl, piperidinyl, pyrazolyl, pyrimidinyl, benzofuranyl, benzothienyl, indolyl, benzimidazolyl, tetrahydroisoquinolinyl, benzotriazolyl, and thiazolyl, said heterocyclic ring system being substituted with 0–2 $R^{10}$; where:

$R^9$, $R^{10}$, $R^{12}$, $R^{15}$ and $R^{16}$ each have the same meaning as set out further above under the definitions of $R^{1-5}$.

In accordance with the process of the present invention, the reaction which takes place between the aromatic compound of Formula (2.0.0) and the secondary nitrile of Formula (3.0.0) is required to be in the presence of a base having a $pK_a$ in the range of from about 17 to about 30, provided that the difference in $pK_a$ numerical values between said base and said corresponding secondary nitrile of Formula (3.0.0) is no more than about 6, and preferably no more than about 4; and in an aprotic solvent having a dielectric constant ($\in$) of less than about 20; and at a temperature in the range of from about 0° C. to about 120° C.

The character of the base which is used in carrying out the process of the present invention is critical to obtaining the acceptable yields of tertiary-nitrile-substituted aromatic compound final product which serves to distinguish the process of the present invention from the processes of the prior art. The relative strength of the base which is used in the process of the present invention should be as close as possible to the relative strength as a base of the secondary nitrile reactant of Formula (3.0.0) which is used in that process. Further, it is desirable to quantify the relative strength of the base which is to be used. Such quantification will permit greater discrimination in selection of the base, as well as permit a more precise comparison of the relative strength of the base to the corresponding relative strength of the secondary nitrile reactant.

In order to quantify the relative strength of the base for use in the process of the present invention, use is made herein of the dissociation constant, $K_a$ of the base and the corresponding secondary nitrile of Formula (3.0.0). The dissociation constant is defined as the equilibrium constant for transfer of a proton from an acid HA to water, and is calculated in accordance with the following equation.

$$K_a = \frac{[H_3O^+][A:^-]}{[HA]}$$

where the values within the brackets are the molar concentrations at equilibrium for the acid and its dissociated constituents. For convenience, dissociation constants are expressed as a negative logarithm, abbreviated p. Thus, $pK_a = -\log K_a$. Stronger acids have larger dissociation constants, but correspondingly smaller $pK_a$ values. A value which can be used to quantify the comparative difference between the strength of the base and corresponding secondary nitrile used in the process of the present invention, will prove to be useful in carrying out said process.

Accordingly, the relative strength of the base A: – and corresponding secondary nitrile in question is conveniently expressed in terms of the $pK_a$ of its conjugate acid HA. Where a base is characterized as being a strong base, the converse is also inherently true, i.e., that its conjugate acid is a weak acid. Thus, $pK_a$ numerical values for the conjugate acids of two or more bases will permit one to readily compare those bases and quickly order them in accordance with which one is the stronger base and which one is the weaker base. The stronger base has the conjugate acid with the higher $pK_a$ numerical value. In the present description of the process of the present invention, a given base will be directly or indirectly stated to have a $pK_a$ numerical value, it being understood that the $pK_a$ numerical value in question is that of the conjugate acid of said base.

The base used in the process of the present invention will preferably have a $pK_a$ numerical value as close to that of the secondary nitrile of Formula (3.0.0) used in that process, as possible. Consequently, based on the $pK_a$ numerical values of the secondary nitrites of Formula (3.0.0) which are suitable for use in the process of the present invention, it is considered to be an essential requirement that the base used in the process of the present invention have a $pK_a$ value in the range of from about 17 to about 30. It is a further requirement that the difference in $pK_a$ numerical values between said base and said corresponding secondary nitrile of Formula (3.0.0) used in the process of the present invention be no more than about 6, and preferably no more than about 4. The secondary nitrile of Formula (3.0.0) used in the process of the present invention has a general chemical structure which may be represented by the following Formula (3.0.1):

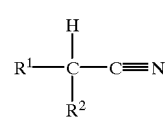
(3.0.1)

where the acidic proton is indicated by bold italics.

A preferred base for use in the process of the present invention which meets the above-described critical requirements is the potassium, sodium or lithium salt of bis (trimethylsilyl)amide, also referred to as hexamethyldisilazane (HMDS). The potassium salt of HMDS is preferred over the sodium or lithium salt, and the sodium salt of HMDS is preferred over the lithium salt. In a preferred embodiment of the process of the present invention, only the potassium and sodium salts of HMDS are employed. The preferred base KHMDS may be represented by Formula (5.0.0):

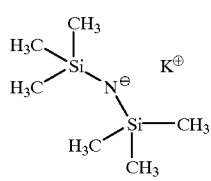

(5.0.0)

Other bases of this type may also be used, e.g., those represented by the following structural Formula (5.0.1):

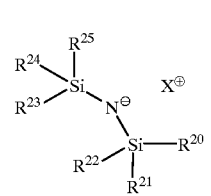

(5.0.1)

wherein $R^{20}$, $R^{21}$, $R^{22}$, $R^{23}$, $R^{24}$, and $R^{25}$ are each independently selected from the group consisting of ($C_1$–$C_5$) alkyl and phenyl; and $X^+$ is a suitable cation, preferably selected from the group consisting of potassium, sodium, and lithium. A preferred base is one where each of $R^{20}$ through $R^{25}$ is methyl, resulting in KHMDS of Formula (5.0.0) above. Another preferred base is that where one R group on each Si atom is tert-butyl while the remaining R groups all have the meaning of methyl, e.g., $R^{21}$ and $R^{24}$ are both tert-butyl and $R^{20}$, $R^{22}$, $R^{23}$, and $R^{25}$ are each methyl. Yet another preferred base is that where two R groups on each Si atom is tert-butyl while the two remaining R groups both have the meaning of phenyl, e.g., and $R^{20}$, $R^{22}$, $R^{23}$, and $R^{25}$ are each tert-butyl and $R^{21}$ and $R^{24}$ are both phenyl.

In accordance with the process of the present invention the type of solvent which is used to carry out the secondary nitrile and aromatic compound reaction represents a choice which is also critical to obtaining acceptable yields of final product. The solvent selected should be aprotic and have a dielectric constant ($\in$) of less than about 20. As is well known, solvents may be classified in accordance with whether or not they are capable of acting as hydrogen bond donors. Those solvents which can be hydrogen bond donors, such as water and alcohols, are classified as protic solvents. Those solvents which cannot be hydrogen bond donors, such as hexane and carbon tetrachloride, are classified as aprotic solvents. In order for a solvent to be suitable for use in the process of the present invention, it must be an aprotic solvent. Thus, toluene and tetrahydrofuran, two of the preferred solvents used in the process of the present invention, are both aprotic solvents.

A other criterion which a solvent must satisfy in order to be found suitable for use in the process of the present invention, is that it must have a dielectric constant ($\in$) of less than about 20. The dielectric constant ($\in$) of a solvent is the quantitative measurement of the ability of the solvent to separate ions. This property is related in an approximate manner to whether a solvent is polar or apolar. Solvents with relatively low dielectric constants ($\in$) are usually apolar solvents; and conversely, solvents with a relatively high dielectric constant ($\in$) are usually polar solvents. An example of a solvent with a high dielectric constant ($\in$) which has been found to be unsuitable for use in the process of the present invention is N-methyl-α-pyrrolidone (NMP), whose $\in$=32.2. As already pointed out, the dielectric constants ($\in$) of toluene and tetrahydrofuran (THF), two of the preferred solvents for use in the process of the present invention, are 2.4 and 7.6, respectively.

As already mentioned, toluene and tetrahydrofuran are examples of suitable solvents for use in the process of the present invention. Other suitable solvents meeting the above-mentioned criteria include, but are not limited to, hexane; benzene; o-, m-, and p-xylene; diethyl ether; diisopropyl ether; methyl tert-butyl ether; and 1,2-dimethoxyethane. Also contemplated to be within the scope of the present invention is the use of a mixture of two or more suitable solvents as above described. It is preferred to use a single solvent by itself, but various conditions may arise which would dictate the use of, or else would make it advantageous to use a mixture of solvents rather than a single solvent alone. Such conditions include but are not limited to solubility problems with regard to the reaction components, desirable adjustments in the temperature at which the process of the present invention is carried out, the availability and cost of the solvents being used; and the separation of the final product from the reaction mixture and its subsequent purification.

The critical nature of the choice of base and solvent, which are contemplated to work together as a base/solvent system in the process of the present invention, has been substantiated by the determination that many such combinations either fail altogether to produce a tertiary-nitrile-substituted aromatic compound final product, or else produce such a final product in unacceptably low yields. For example, it has been found that by using a base/solvent system comprising potassium bis(trimethylsilyl)amide (KHMDS) as the base and either toluene or tetrahydrofuran (THF) as the solvent, that it is possible to produce a tertiary-nitrile-substituted aromatic compound final product in accordance with the present invention in yields of 85% or greater by weight, frequently 90% or greater by weight, and often 95% or greater by weight, based on the weight of the reaction components.

The expression "unacceptably low yields" has been used herein to contrast the unexpectedly superior results obtained with the process of the present invention to the unsatisfactory results obtained with the processes of the prior art. It will be understood that the surprising improvement in yields achieved by use of the process of the present invention need not always be reflected solely in very high yield percentages, per se. Thus, it may be the case that for a given final product of Formula (1.0.0) the prior art processes are inoperative, resulting in a 0% yield, or else said prior art processes provide said final product in extremely low yields. Accordingly, it will be appreciated that a 25% yield obtained using the process of the present invention may constitute an unexpected improvement over the results obtained using the processes of the prior art where said processes provide, e.g., a 0% or >1% yield of the same final product. Percentage yields obtained using the process of the present invention are described in detail elsewhere herein.

Instances of such failures of prior art processes to yield any final product abound. For example, when the base being used is lithium diisopropylamide (LDA), even though the solvent being used is tetrahydrofuran (THF), which would otherwise be suitable, decomposition of the initial reaction mixture occurs. Similarly, where the base/solvent system utilized is potassium tert-butyloxide (t-BuOK) in tetrahydrofuran (THF), decomposition of the initial reaction mixture occurs. Where the base being used is chosen from cesium, sodium, or potassium carbonate ($CsCO_3$, $Na_2CO_3$, or $K_2CO_3$, respectively) and the solvent being used is tetrahydrofuran (THF), no reaction takes place at all.

The solvent component of the base/solvent system is also critical to obtaining acceptable results. For example, where the base selected is potassium bis(trimethylsilyl)amide (KHMDS), which would otherwise be suitable, and the solvent selected is dimethylsulfoxide (DMSO), no reaction at all takes place. Further, where the base is potassium bis(trimethylsilyl)amide (KHMDS) and the solvent is N-methyl-α-pyrrolidone NMP), the process results in an aromatic compound substituted by tertiary nitrile final product in unacceptably low yields of about 5% or less by weight, based on the weight of the reaction components.

The choice of the temperature at which the reaction mixture containing the tertiary nitrile and substituted aromatic compound is to be maintained in accordance with the process of the present invention, is of less critical importance than the choice of the above-mentioned base and solvent system. However, the proper reaction temperature is essential to obtaining acceptable yields of tertiary-nitrile-substituted aromatic compound final product in accordance with the present invention, and should fall within the range of from about 0° C. to about 120° C., preferably in the range of from about 20° C. to about 110° C., more preferably in the range of from about 30° C. to about 105° C., and most preferably in the range of from about 40° C. to about 100° C. The choice of temperature at which the reaction in accordance with the process of the present invention is carried out will impact, along with other factors, the amount of time required to carry said reaction to a reasonable stage of completion. It has been found that, as a general matter, where the temperatures employed in carrying out the process are within the above-stated ranges, and particularly within the above-stated preferred, more preferred and most preferred ranges, that the process of the present invention will be reasonably complete within the range of from about 0.1 hour to about 50 hours, more likely within the range of from about 0.5 hour to about 30 hours, and most likely within the range of from about 1 hour to about 18 hours The preparation process of the present invention may be represented by the following reaction scheme:

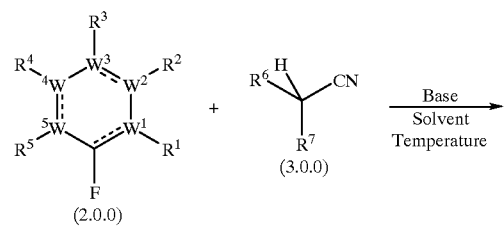

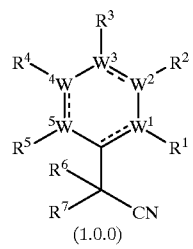

In the above reaction scheme, the starting material of Formula (2.0.0) is reacted with a secondary nitrile of Formula (3.0.0) in the presence of a base such as potassium bis(trimethylsilyl)amide (KHMDS) in a solvent such as toluene, tetrahydrofuran, diethyl ether, diisopropyl ether, methyl tert-butyl ether, 1,2-dimethoxy ethane, or a mixture of the aforementioned solvents, preferably toluene or tetrahydrofuran, at a temperature between 0° C. and 120° C., preferably between 40° C. and 100° C., to provide a final product of Formula (1.0.0).

These preferred embodiments of the process of the present invention are further demonstrated in the working examples set forth below. These examples are intended to be illustrative of the present invention and are not for the purpose of, and should not be taken as in any way limiting the scope or content of the process of the present invention. The claims appended to the instant specification should be consulted for a definition of the scope and content of the present invention.

EXAMPLE 1

To a solution of an aryl fluoride of Formula (2.0.0) in toluene (10 volumes) was added a nitrile of Formula (3.0.0), the number of equivalents of which are indicated in Table 1 below; and a 0.5 M solution of potassium bis(trimethylsilyl) amide in toluene, the number of equivalents of which are indicated in Table 1 below. Each reaction mixture was stirred at a temperature and for an amount of time also indicated in Table 1 below, after which each said reaction mixture was cooled to room temperature, poured into 1N HCl, and thereafter extracted with toluene. The organic extracts were washed with water, dried over magnesium sulfate, filtered and concentrated. The crude product was purified by chromatography on silica gel to afford the desired product of Formula (1.0.0) in the yield indicated in Table 1 below.

EXAMPLES 2 THROUGH 19

To a solution of an aryl fluoride of Formula (2.0.0) in tetrahydrofuran (10 volumes) was added a nitrile of Formula (3.0.0), the number of equivalents of which are indicated in Table 1 below; and potassium bis(trimethylsilyl)amide, the number of equivalents of which are indicated in Table 1 below. Each reaction mixture was stirred at a temperature and for an amount of time indicated in Table 1 below, after which each said reaction mixture was cooled to room temperature, poured into 1N HCl, and thereafter extracted with methyl tert-butyl ether. The organic extracts were washed with water, dried over magnesium sulfate, filtered and concentrated. The crude product was purified by chromatography on silica gel to afford the desired product of Formula (1.0.0) in the yield indicated in Table 1 below.

TABLE 1

| Exp. No. | Product Formula | Solvent | T(° C.) | Time | KHMDS (equiv.) | R⁶R⁷CHCN (equiv.) | Yield (%) |
|---|---|---|---|---|---|---|---|
| 2 | (1.1.0) | Toluene | 60 | 40 min | 1.5 | 3.3 | 94 |
| 3 | (1.1.1) | Toluene | 60 | 40 min | 1.5 | 4.0 | 83 |
| 4 | (1.1.2) | Toluene | 100 | 3 h | 1.5 | 4.1 | 69 |
| 5 | (1.1.3) | Toluene | 60 | 45 min | 1.5 | 4.0 | 77 |
| 6 | (1.1.4) | Toluene | 70 | 48 h | 1.5 | 4.0 | 85 |
| 7 | (1.1.5) | Toluene | 70 | 10 min | 1.5 | 3.9 | 72 |
| 8 | (1.1.6) | THF | 60 | 50 h | 1.5 | 4.0 | 66 |
| 9 | (1.1.7) | Toluene | 60 | 18 h | 1.5 | 4.0 | 95 |
| 10 | (1.1.8) | Toluene | R.T. | 5 h | 1.5 | 2.0 | 24 |
| 11 | (1.1.9) | THF | 75 | 2 h | 1.5 | 4.0 | 72 |
| 12 | (1.1.10) | THF | 75 | 14 h | 1.5 | 4.0 | 71 |
| 13 | (1.1.11) | THF | 75 | 14 h | 1.5 | 4.0 | 69 |
| 14 | (1.1.12) | Toluene | 75 | 48 h | 1.5 | 4.0 | 47 |
| 15 | (1.1.13) | THF | 75 | 24 h | 1.5 | 4.0 | 67 |
| 16 | (1.1.14) | THF | 75 | 30 h | 1.5 | 4.0 | 35 |
| 17 | (1.1.15) | THF | 75 | 27 h | 1.5 | 4.0 | 30 |
| 18 | (1.1.16) | THF | 75 | 15 min | 1.5 | 4.0 | 70 |
| 19 | (1.1.17) | THF | 80 | 4 h | 1.5 | 4.0 | 28 |

EXAMPLE 2

2-Methyl-2-(4-trifluoromethyl-phenyl)-propionitrile (1.1.0)

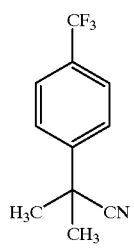

(1.1.0)

Purified by chromatography on silica gel (ethyl acetate/hexanes 15/85).

$^1$H NMR (400 MHz, CDCl$_3$) δ1.73 (s, 6), 7.59 (d, 2, J=9.0), 7.64 (d, 2, J=9.0). $^{13}$C NMR (100 MHz, CDCl$_3$) δ28.90, 37.25, 123.12 (q, J=272.7), 123.75, 125.64, 125.93, 130.15 (q, J=33.2), 145.38.

IR 2988, 2239, 1622, 1415, 1330, 1170, 1128, 1069, 842 cm$^{-1}$.

Analysis calculated for C$_{11}$H$_{10}$F$_3$N: C, 61.97; H, 4.73; N, 6.57. Found: C, 61.91; H, 4.96; N, 6.61.

EXAMPLE 3

4-(Cyano-dimethyl-methyl)-benzonitrile 1.1.1)

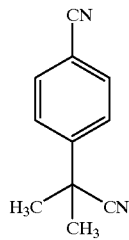

(1.1.1)

Purified by filtration on a pad of silica gel eluting with ethyl acetate, Mp=88–89° C.

$^1$H NMR (300 MHz, CDCl$_3$) δ1.78 (s, 6), 7.64 (d, 2, J=8.1), 7.74 (d, 2, J=8.3). $^{13}$C NMR (100 MHz, CDCl,) δ28.87, 37.49, 112.06, 118.19, 123.32, 126.08, 132.85, 146.48.

IR (CHCl$_3$) 2989, 2233, 1611, 1505, 1463, 1408, 1371, 1100, 838 cm$^{-1}$.

Analysis calculated for C$_{11}$H$_{10}$N$_2$: C, 77.62; H, 5.92; N, 16.46. Found: C, 77.26; H, 5.90; N, 16.52.

EXAMPLE 4

2-(3-Methoxy-phenyl)-2-methyl-propionitrile(1.1.2)

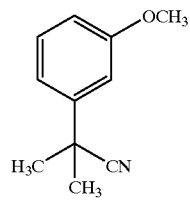

(1.1.2)

Purified by chromatography on silica gel (ethyl acetate/hexanes 10/90).

$^1$H NMR (300 MHz, CDCl$_3$) δ1.75 (s, 6), 3.86 (s, 3), 6.88 (dd, 1, J=2.5, 8.3), 7.04–7.06 (m, 1), 7.07–7.11 (m, 1), 7.34 (t, 1, J=8.3). $^{13}$C NMR (100 MHz, CDCl$_3$) δ29.02, 37.09, 55.24, 111.40, 112.60, 117.23, 124.41, 129.91, 142.93, 159.83.

IR 2983, 2940, 2236, 1602, 1586, 1489, 1463, 1434, 1294, 1268, 1048, 782 cm$^{-1}$.

Analysis calculated for C$_{11}$H$_{13}$NO; C, 75.40; H, 7.48; N, 7.99. Found: C, 75.61; H, 7.67; N, 7.86.

EXAMPLE 5

2-(2-Chloro-phenyl)-2-methyl-propionitrile (1.1.3)

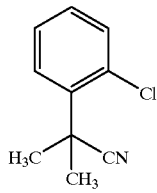

(1.1.3)

Purified by chromatography on silica gel (ethyl acetate/hexanes 10/90).

$^1$H NMR (300 MHz, CDCl$_3$) δ1.91 (s, 6), 7.29–7.34 (m, 2), 7.46–7.53 (m, 2). $^{13}$C NMR (100 MHz, CDCl$_3$) δ27.19, 36.24, 123.50, 127.00, 127.33, 129.41, 131.92, 133.31, 136.95.

IR 2984, 2236, 1473, 1432, 1234, 1043, 759 cm$^{-1}$.

Analysis calculated for C$_{10}$H$_{10}$ClN. C, 66.86; H, 5.61; N, 7.80. Found: C, 67.22; H, 5.64; N, 7.63.

EXAMPLE 6

2-(3,5-Dimethoxy-phenyl)-2-methyl-propionitrile (1.1.4)

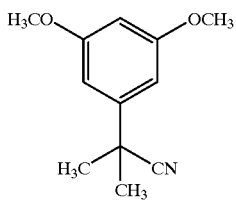

(1.1.4)

Purified by chromatography on silica gel (ethyl acetate/hexanes 15/85).

$^1$H NMR (300 MHz, CDCl$_3$) δ1.74 (s, 6), 3.85 (s, 6), 6.43 (t, 1, J=2.2), 6.64 (d, 2J=2.2). $^{13}$C NMR (100 MHz, CDCl$_3$) δ29.06, 37.34, 55.44, 99.12, 103.63, 124.44, 143.81, 161.10.

IR 2982, 2939, 2236, 1598, 1459, 1427, 1207, 1159, 1067, 1052, 696cm$^{-1}$.

Analysis calculated for C$_{12}$H$_{15}$NO$_2$. C, 70.22; H, 7.37; N, 6.82. Found: C, 70.17; H, 7.65; N, 6.96.

EXAMPLE 7

2-Methyl-2-(4-methyl-pyridin-2-yl)-propionitrile (1.1.5)

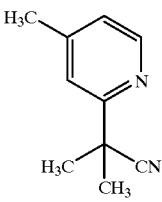

(1.1.5)

Purified by chromatography on silica gel (ethyl acetate/hexanes 20/80).

$^1$H NMR (300 MHz, CDCl$_3$) δ1.77 (s, 6), 2.41 (s, 3), 7.08 (dd, 1, J=0.8, 5.0), 7.43 (d, 1, J=0.8), 8.47 (d, 1, J=5.0). $^{13}$C NMR (75 MHz, CDCl$_3$) δ22.39, 29.06, 40.54, 121.98, 24.89, 125.66, 149.79, 150.48, 160.55.

IR 2982, 2238, 1605, 1478, 1130, 995, 830 cm$^{-1}$.

Analysis calculated for C$_{10}$H$_{12}$N$_2$: C, 74.97; H, 7.55; N, 17.48. Found: C, 74.96; H, 7.85; N, 17.45.

EXAMPLE 8

2-(4-Methoxy-phenyl)-2-methyl-propionitrile (1.1.6)

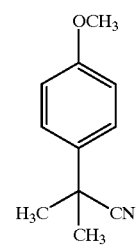

(1.1.6)

Purified by chromatography on silica gel (ethyl acetate/hexanes 20/80).

$^1$H NMR (300 MHz, CDCl$_3$) δ1 74 (s, 6), 3.85 (s, 3), 6.94 (d, 2, J=8.9), 7.42 (d, 2, J=8.9). $^{13}$C NMR (100 MHz, CDCl$_3$) δ29.25, 36.44, 55.34, 114.19, 124.82, 126.25, 133.50, 159.02.

IR 2982, 2235, 1513, 1256, 1186, 1033, 831 cm$^{-1}$.

Analysis calculated for C$_{11}$H$_{13}$NO: C, 75.40; H, 7.48; N, 7.99. Found: C, 75.48; H, 7.55; N, 8.10.

EXAMPLE 9

2-(2-Methoxy-phenyl)-2-methyl-propionitrile (1.1.7)

(1.1.7)

Purified by chromatography on silica gel (ethyl acetate/hexanes 20/80).

$^1$H NMR (300 MHz, CDCl$_3$) δ1.80 (s, 6), 3.96 (s, 3), 6.97–7.02 (m, 2), 7.29–7.39 (m, 2). $^{13}$C NMR (100 MHz, CDCl$_3$) δ27.00, 34.43, 55.51, 112.02, 120.76, 124.80, 125.92, 128.62, 29.39, 157.30.

IR 2980, 2235, 1493, 1462, 1437, 1253, 1027, 756 cm$^{-1}$.

Analysis calculated for C$_{11}$H$_{13}$NO: C, 75.40; H, 7.48; N, 7.99. Found: C, 75.29; H, 7.30; N, 8.25.

EXAMPLE 10

1-(2-Chloro-phenyl)-cyclopropanecarbonitrile (1.1.8)

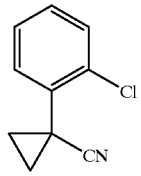
(1.1.8)

Purified by chromatography on silica gel (ethyl acetate/hexanes 20/80).

$^1$H NMR (300 MHz, CDCl$_3$) δ1.28–1.38 (m, 2), 1.71–1.75 (m, 2), 7.21–7.43 (m, 4). $^{13}$C NMR (100 MHz, CDCl$_3$) δ13.17, 16.27, 121.78, 127.16, 130.07, 131.16, 133.60, 136.54.

IR 3063, 3020, 2235, 1477, 1435, 1051, 1033, 759 cm$^{-1}$.

Analysis calculated for C$_{11}$H$_8$ClN; C, 67.62; H, 4.54; N, 7.89. Found: C, 67.35; H, 4.58; N, 7.88.

EXAMPLE 11

2-(4-Chloro-phenyl)-2-methyl-propionitrile (1.1.9)

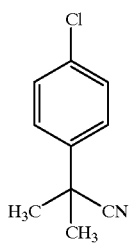
(2.0.11)

Purified by chromatography on silica gel (ethyl acetate/hexanes 10/20).

$^1$H NMR (300 MHz, CDCl$_3$) δ1.75 (s, 6), 7.39 (d, 2, J=9.0), 7.45 (d, 2, J=8.9). $^{13}$C NMR (100 MHz, CDCl$_3$) d 30.34, 38.06, 125.34, 127.80, 130.33, 135.03, 141.22.

IR 2984, 2237, 1495, 1106, 1013, 828 cm$^{-1}$.

Analysis calculated for C$_{10}$H$_{10}$ClN. C, 66.86; H, 5.61; N, 7.80. Found: C, 66.51; H, 5.83; N, 7.74.

EXAMPLE 12

2-Methyl-2-m-tolyl-propionitrile (1.1.10)

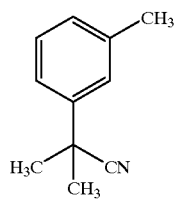
(1.1.10)

Purified by chromatography on silica gel (ethyl acetate/hexanes 10/90).

$^1$H NMR (300 MHz, CDCl$_3$) δ1.75 (s, 3), 2.42 (s, 3), 7.14–7.18 (m, 1), 7.27–7.18 (m, 3). $^{13}$C NMR (75 MHz, CDCl$_3$) δ22.81, 30.42, 38.35, 123.26, 125.95, 127.13, 129.80, 130.09, 139.94, 142.61.

IR 2983, 2237, 1607, 1490, 1461, 1368, 1198, 1090, 787 cm$^{-1}$.

Analysis calculated for C$_{11}$H$_{13}$N: C, 82.97; H, 8.23; N, 8.80. Found: C, 82.97; H. 8.23; N, 8.80.

EXAMPLE 13

1-(2-Methyl-2-phenyl-propionitrile (1.1.11)

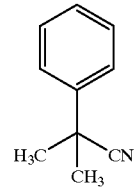
(1.1.11)

Purified by chromatography on silica gel (ethyl acetate/hexanes 10/90).

$^1$H NMR (300 MHz, CDCl$_3$) δ1.76 (s, 3), 7.35–7.53 (m, 5). $^{13}$C NMR (100 MHz, CDCl$_3$) δ29.15, 37.16, 124.55, 125.05, 127.79, 128.94, 141.42.

IR 2983, 2237, 1495, 1448, 764 cm$^{-1}$.

Analysis calculated for C$_{10}$H$_{11}$N: C, 82.72; H, 7.64; N, 9.65. Found: C, C, 82.76; H, 7.90; N,9.88.

EXAMPLE 14

1-(2-Methoxy-phenyl)-cyclopropanecarbonitrile (1.1.12)

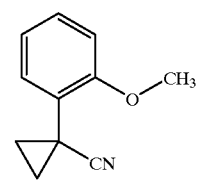
(1.1.12)

Purified by chromatography on silica gel (ethyl acetate/hexanes 10/90 to provide an oil which crystallized upon standing); Mp=49–59° C.

$^1$H NMR (300 MHz, CDCl$_3$) δ1.26–1.30 (m, 2), 1.61–1.66 (m, 2), 3.97 (s, 3), 6.92–6.97 (m, 2), 7.24 (dd, 1, J=7.9, 1.7), 7.29–7.37 (m, 1). $^{13}$C NMR (100 MHz, CDCl$_3$) δ10.18, 15.24, 55.61, 110.89, 120.38, 123.08, 124.07, 129.82, 129.92, 158.97.

IR 2234, 1496, 1465, 1248, 1026, 756 cm$^{-1}$.

Analysis calculated for C$_{11}$H$_{11}$NO: C, 76.28; H, 6.40; N, 8.09. Found: C, 76.28; H, 6.40; N, 8.09.

EXAMPLE 15

(2S)-2-(2-Methoxy-phenyl)-bicyclo[2.2.1]hept-5-ene-2-carbonitrile (1.1.13)

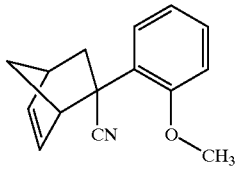

(1.1.13)

Purified by filtration on a pad of silica gel (ethyl acetate/hexanes 35/65 to provide an oil which was crystallized from ethanol); Mp=$_{135-137}$° C.

$^1$H NMR (400 MHz, CDCl$_3$) δ1.52 (d, 1, J=9.0), 1.61–1.64 (m, 1), 2.02 (dd, 1, J=12.6, 3.46), 2.21 (dd, 1, J=11.8, 2.8), 2.99 (bs, 1), 3.62 (bs, 1), 3.91 (s, 3), 6.40 (dd, 1, J=5.8, 3.0), 6.67 (dd, 1, J=5.8, 3.0), 6.91–6.96 (m, 2), 7.24–7.30 (m, 2). $^{13}$C NMR (100 MHz, CDCl$_3$) δ41.42, 43.13, 43.68, 46.90, 48.41, 55.60, 111.66, 120.41, 124.51, 125.36, 129.02, 129.38, 134.44, 140.87, 158.08.

IR (KBr) 2990, 2977, 2226, 1597, 1489, 1439, 1248, 1023, 764, 723 cm$^{-1}$.

Analysis calculated for C$_{15}$H$_{15}$NO: C, 79.97; H, 6.71; N, 6.22. Found: C, 79.97; H, 6.71; N, 6.22.

EXAMPLE 16

2-(4'-Bromo-biphenyl-4-yl)-2-methyl-propionitrile (1.1.14)

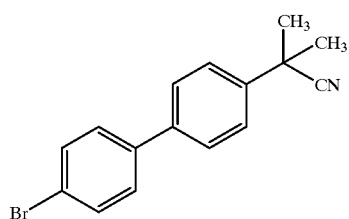

(1.1.14)

Purified by chromatography on silica gel (ethyl acetate/hexanes 10/90); Mp=111–112° C.

$^1$H NMR (400 MHz, CDCl$_3$) δ1.76 (s, 6), 7.44 (dd, 2, J=6.6, 1.9), 7.52–7.57 (m, 6). $^{13}$C NMR (100 MHz, CDCl$_3$) δ29.13, 39.98, 121.90, 124.38, 125.68, 127.40, 128.64, 131.98, 139.13, 139.57, 140.86.

IR (KBr) 2986, 2235, 1483, 1461, 1105, 815 cm$^{-1}$.

Analysis calculated for C$_{16}$H$_{14}$BrN: C, 64.02; H, 4.70; N, 4.67. Found: C, 64.27; H, 4.70; N,4.58.

EXAMPLE 17

1-(4'-Bromo-biphenyl-4-yl)-cyclohexane-1,4-dicarbonitrile (1.1.15)

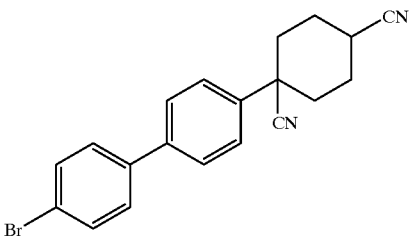

(1.1.15)

Purified by chromatography on silica gel (IPE/CH$_2$Cl$_2$/Hexanes 25/25/50) to provide the product as a 1:1 mixture of diastereoisomers; Mp=211° C.

$^1$H NMR (400 MHz, CDCl$_3$) δ1.84–2.62 (m, 8), 3.15 (bs, 1), 7.41–7.62 (m, 8). $^{13}$CNMR (100 MHz, CDCl$_3$) δ25.82, 25.92, 26.41, 27.24, 33.12, 35.74, 42.79, 43.52, 120.88, 121.11, 121.20, 121.47, 122.05, 122.11, 126.00, 126.10, 127.63, 128.62, 128.65, 132.02, 138.82, 138.91, 139.00, 140.17, 140.25.

IR (KBr) 2945, 2235, 1484, 1455, 1388, 1081, 1003, 812 cm$^{-1}$.

Analysis calculated for C$_{20}$H$_{17}$BrN$_2$: C, 65.76; H, 4.69; N. 7.67. Found: C, 65.76; H, 4.65; N, 7.67.

EXAMPLE 18

(2S)-2-(2-Methoxy-phenyl)-bicyclo[2.2.1]heptane-2-carbonitrile(1.1.16)

(1.1.16)

Purified by chromatography on silica gel (ethyl acetate/hexanes 5/95); Mp=87–88° C.

$^1$H NMR (400 MHz, CDCl$_3$) δ1.30–1.48 (m, 2), 1.52 (d, 1, J=10.0), 1.60–1.80 (m, 2), 1.98 (dt, 1, J=13.5, 3.5), 2.12–2.18 (m, 1), 2.23 (dd, 1, J=13.5, 2.4), 2.33 (s, 1), 2.97 (d,1, J=3.6), 3.91 (s, 3), 6.89–6.94 (m, 2), 7.24–7.28 (m, 2). $^{13}$C NMR (100 MHz, CDCl$_3$) δ25.99, 28.64, 37.02, 37.09, 37.41, 42.97, 46.67, 55.58, 111.99, 120.14, 124.16, 125.26, 128.86, 129.68, 157.48.

IR (KBr) 2971, 2225, 1597, 1491, 1251, 1026, 764 cm$^{-1}$.

Analysis calculated for C$_{15}$H$_{175}$NO: C, 79.26; H, 7.54; N, 6.16. Found: C, 79.08; H, 7.58; N, 6.19.

EXAMPLE 19

2-(3,4-Dimethoxy-phenyl)-2-methyl-propionitrile (1.1.17)

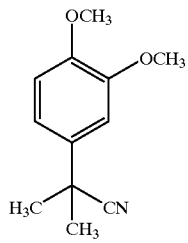

(1.1.17)

Purified by high-pressure liquid chromatography (hexanes/2-propanol 95/5) using a Chiracel OJ column (5 cm×25 cm).

$^1$H NMR (300 MHz, CDCl$_3$) δ1.75 (s, 6), 3.92 (s, 3), 3.95 (s, 3), 8.89 (d, 1, J=8.1), 7.01 (s, 1), 7.03 (d, 1, J=7.9). $^{13}$C NMR (100 MHz, CDCl$_3$) δ29.24, 36.73, 55.95, 55.98, 108.71, 111.16, 117.06, 124.73, 133.94, 148.52, 149.06.

What is claimed is:

1. A process of preparing a tertiary-nitrile-substituted aromatic compound final product of Formula (1.0.0):

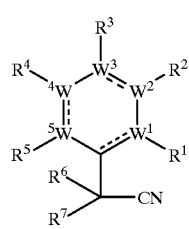

(1.0.0)

comprising treating an aromatic compound of Formula (2.0.0):

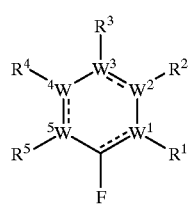

(2.0.0)

with a secondary nitrile of Formula (3.0.0):

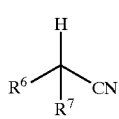

(3.0.0)

in the presence of a base having a pK$_a$ numerical value in the range of from about 17 to about 30, provided that the difference in pK$_a$ numerical values between said base and corresponding secondary nitrile of Formula (3.0.0) is not more than about 6; in an aprotic solvent having a dielectric constant (∈) of less than about 20; and at a reaction temperature in the range of from about 0° C. to about 120° C.; whereby there is formed said tertiary-nitrile-substituted aromatic compound final product of Formula (1.0.0);

wherein the dashed lines, constituent parts W$^1$, W$^2$, W$^3$, W$^4$, and W$^5$; and substituent moieties R$^1$, R$^2$, R$^3$, R$^4$, R$^5$, R$^6$, and R$^7$ wherever they appear in the above-recited compounds of Formulas (1.0.0), (2.0.0) and (3.0.0), all have the following meanings:

(I) each of the dashed lines is independently absent or a bond, so that single or double bonds result at the respective positions of an aromatic compound of Formula (1.0.0) or (2.0.0), provided that at least one of said dashed lines is a bond;

(II) W$^1$, W$^2$, W$^3$, W$^4$, and W$^5$ is each C (carbon) and the dashed line associated therewith is a bond, (III) R$^1$, R$^2$, R$^3$, R$^4$, and R$^5$ is each independently selected so that when the corresponding W$^{1-5}$ is C, said R$^{1-5}$ is a member independently selected from the group consisting of hydrogen; halogen selected from Cl, Br, and I; —N(R$^{12}$)$_2$; —SR$^{12}$; —OR$^{12}$; (C$_1$–C$_6$) alkyl substituted with 0–3 R$^9$, —N(R$^{12}$)$_2$, —SR$^{12}$, or —OR$^{12}$; (C$_2$–C$_6$) alkenyl substituted with 0–3 R$^9$; (C$_3$–C$_6$) alkynyl substituted with 0–3 R$^9$; a (C$_3$–C$_{14}$) carbocyclic ring system substituted with 0–3 R$^9$ or 0–3 R$^{10}$; a heterocyclic ring system independently selected from the group consisting of furanyl, thienyl, pyrrolyl, imidazolyl, pyridyl, pyrazolyl, pyrimidinyl, benzofuranyl, benzothienyl, indolyl, benzimidazolyl, tetrahydroisoquinolinyl, benzotriazolyl, and thiazolyl, said heterocyclic ring system being substituted with 0–2 R$^{10}$; and any two R$^{1-5}$ attached to adjacent carbon atoms taken together to form a 3- or 4-carbon chain forming a fused 5- or 6-membered ring, or a carbon-nitrogen-nitrogen chain forming an indazolyl fused ring, both of said rings being optionally substituted on any aliphatic carbon atoms thereof with a member selected from the group consisting of halogen selected from Cl, Br, and I; (C$_1$–C$_4$) alkyl; (C$_1$–C$_4$) alkoxy; and —NR$^{15}$R$^{16}$; where:

(A) R$^9$ is a member independently selected from the group consisting of hydrogen; cyano; —CH$_2$NR$^{15}$R$^{16}$; —NR$^{15}$R$^{16}$; —R$^{15}$; —OR$^{15}$; (C$_2$–C$_6$) alkenyl; (C$_3$–C$_7$) cycloalkyl; (C$_3$–C$_6$) cycloalkylmethyl; phenethyl; phenoxy; benzyloxy; (C$_3$–C$_6$) cycloalkoxy, (C$_1$–C$_4$) alkyl substituted by a member selected from the group consisting of methylenedioxy, ethylenedioxy, phenyl(C$_1$–C$_3$) alkyl, and a (C$_5$–C$_{14}$) carbocyclic residue; and a 5- to 10-membered heterocyclic ring system containing 1 to 4 heteroatoms independently selected from oxygen, nitrogen, and sulfur, substituted with 0 to 3 substituents R$^{15}$; where:

(1) R$^{15}$ is a member selected from the group consisting of phenyl substituted by 0–3 R$^{11}$; benzyl substituted by 0–3 R$^{11}$; (C$_1$–C$_6$) alkyl substituted by 0–3 R$^{11}$; (C$_2$–C$_4$) alkenyl substituted by 0–3 R$^{11}$; and (C$_2$–C$_6$) alkoxyalkyl substituted by 0–3 R$^{11}$;

where R$^{11}$ is a member independently selected from the group consisting of cyano; —CH$_2$NR$^{18}$R$^{19}$; —NR$^{18}$R$^{19}$; (C$_3$–C$_6$) alkoxyalkyl; (C$_1$–C$_4$) alkyl; (C$_2$–C$_4$) alkenyl; (C$_3$–C$_{10}$) cycloalkyl; (C$_3$–C$_6$) cycloalkylmethyl; benzyl; phenethyl; phenoxy; benzyloxy; (C$_7$–C$_{10}$) arylalkyl; (C$_3$–C$_6$) cycloalkoxy; methylenedioxy; ethylenedioxy; and a (C$_5$–C$_{14}$) carbocyclic residue;

and a 5- to 10-membered heterocyclic ring system containing 1 to 4 heteroatoms independently selected from oxygen, nitrogen, and sulfur;

where $R^{18}$ and $R^{19}$ are each independently selected from the group consisting of $(C_1-C_6)$ alkyl; and phenyl substituted with 0–3 $R^{11}$;

(2) $R^{16}$ is a member selected from the group consisting of $(C_1-C_4)$ alkyl substituted by 0–3 groups selected from the group consisting of $(C_1-C_4)$ alkoxy; $(C_2-C_6)$ alkoxyalkyl; $(C_2-C_6)$ alkenyl; phenyl; and benzyl;

(B) $R^{10}$ when a substituent on a carbon atom, is a member independently selected from the group consisting of phenyl; benzyl; phenethyl; phenoxy; benzyloxy; halogen; cyano; $(C_1-C_4)$ alkyl; $(C_3-C_7)$ cycloalkyl; $(C_3-C_6)$ cycloalkylmethyl; $(C_1-C_6)$ alkoxy; $(C_1-C_4)$ alkoxy$(C_1-C_3)$ alkyl; $(C_3-C_6)$ cycloalkoxy; $(C_1-C_6)$ alkylthio; $(C_1-C_4)$ alkylthio $(C_1-C_3)$ alkyl; —$OR^{15}$; —$NR^{15}R^{16}$; $(C_1-C_4)$ alkyl substituted by —$NR^{15}R^{16}$; $(C_2-C_6)$ alkoxyalkylene optionally substituted by $Si[(C_1-C_3)$ alkyl$]_3$; methylenedioxy; ethylenedioxy; —$S(O)_mR^{15}$; —$SO_2NR^{15}R^{16}$; —$OCH_2CO_2R^{15}$; —$C(R^{16})$=N $(OR^{16})$; and a 5- or 6-membered heterocyclic ring system containing from 1 to 4 heteroatoms selected from oxygen, nitrogen, and sulfur; or $R^{10}$ when a substituent on a nitrogen atom, is a member independently selected from the group consisting of phenyl; benzyl; phenethyl; $(C_1-C_4)$ alkyl; $(C_1-C_4)$ alkoxy; $(C_3-C_6)$ cycloalkyl; $(C_3-C_6)$ cycloalkylmethyl; $(C_2-C_6)$ alkoxyalkyl; —$CH_2NR^{15}R^{16}$; —$NR^{15}R^{16}$; and —$C(R^{16})$=N $(OR^{16})$;

where $R^{15}$ and $R^{16}$ have the same meaning as recited further above;

(C) $R^{12}$ is a member selected from the group consisting of $(C_1-C_6)$ alkyl substituted )y 0–3 $R^9$; and $(C_3-C_6)$ alkoxyalkyl substituted by 0–3 $R^9$; and where $R^9$ has the same meaning as recited further above;

(IV) $R^6$ and $R^7$ are each independently selected from the group consisting of $(C_1-C_6)$ alkyl substituted with 0–3 $R^9$; —$N(R^{12})_2$; —$SR^{12}$; —$OR^{12}$; $(C_2-C_6)$ alkenyl substituted with 0–3 $R^9$; $(C_3-C_6)$ alkynyl substituted with 0–3 $R^9$; a $(C_3-C_{14})$ carbocyclic ring system substituted with 0–3 $R^9$ or 0–3 $R^{10}$; and a heterocyclic ring system independently selected from the group consisting of furanyl, thienyl, pyrrolyl, imidazolyl, tetrahydropyranyl, pyridyl, piperidinyl, pyrazolyl, pyrimidinyl, benzofuranyl, benzothienyl, indolyl, benzimidazolyl, tetrahydroisoquinolinyl, benzotriazolyl, and thiazolyl, said heterocyclic ring system being substituted with 0–2 $R^{10}$; or $R^6$ and $R^7$ are taken together to form a $(C_3-C_{14})$ carbocyclic ring system substituted with 0–3 $R^9$ or 0–3 $R^{10}$; phenyl; 1- or 2-naphthyl substituted with 0–3 $R^9$ or 0–3 $R^{10}$; or a heterocyclic ring system independently selected from the group consisting of furanyl, thienyl, pyrrolyl, imidazolyl, tetrahydropyranyl, pyridyl, piperidinyl, pyrazolyl, pyrimidinyl, benzofuranyl, benzothienyl, indolyl, benzimidazolyl, tetrahydroisoquinolinyl, benzotriazolyl, and thiazolyl, said heterocyclic ring system being substituted with 0–2 $R^{10}$; where:

$R^9$, $R^{10}$, $R^{12}$, $R^{15}$ and $R^{16}$ each have the same meaning as set out further above under the definitions of $R^{1-5}$.

2. A process according to claim 1 wherein the difference in $pK_a$ numerical values between said base and said corresponding secondary nitrile of Formula (3.0.0) is no more than about 4.

3. A process according to claim 1 wherein said base is a compound of Formula (5.0.1):

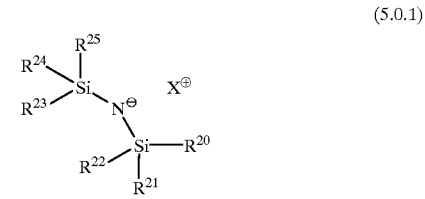

(5.0.1)

wherein $R^{20}$, $R^{21}$, $R^{22}$, $R^{23}$, $R^{24}$, and $R^{25}$ are each independently selected from the group consisting of $(C_1-C_5)$ alkyl and phenyl; and $X^+$ is a suitable cation.

4. A process according to claim 3 wherein said suitable cation is a member selected from the group consisting of potassium, sodium, and lithium.

5. A process according to claim 3 wherein for said base of Formula (5.0.1), one R group on each Si atom is tert-butyl while the remaining R groups all have the meaning of methyl.

6. A process according to claim 3 wherein for said base of Formula (5.0.1), two R groups on each Si atom are tert-butyl while each remaining R group on each Si atom has the meaning of phenyl.

7. A process according to claim 1 wherein said base is the potassium, sodium or lithium salt of bis(trimethylsilyl) amide (KHMDS).

8. A process according to claim 7 wherein said base is the potassium salt of HMDS of Formula (5.0.0):

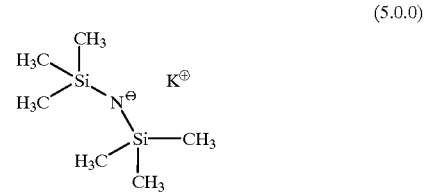

(5.0.0)

9. A process according to claim 1 wherein said solvent is a member selected from the group consisting of toluene; tetrahydrofuran; hexane; benzene; o-, m-, and p-xylene; diethyl ether; diisopropyl ether; methyl tert-butyl ether; 1,2-dimethoxyethane; and mixtures comprising one or more of said above-recited solvents.

10. A process according to claim 1 wherein the base/solvent system employed therein comprises the potassium salt of bis(trimethylsilyl)amide (KHMDS) as the base and toluene or tetrahydrofuran (THF) as the solvent.

* * * * *